United States Patent [19]

Kligman

[11] Patent Number: 5,134,163

[45] Date of Patent: Jul. 28, 1992

[54] METHODS OF PREVENTING AND REDUCING THE SIZE OF STRIAE DISTENSAE LESIONS

[76] Inventor: Albert M. Kligman, 637 Pine St., Philadelphia, Pa. 19106

[21] Appl. No.: 402,271

[22] Filed: Sep. 1, 1989

[51] Int. Cl.$^5$ .............................................. A61K 31/20
[52] U.S. Cl. ..................................... 514/559; 514/725
[58] Field of Search ................................. 514/559, 721

[56] References Cited

U.S. PATENT DOCUMENTS 4,603,146  7/1986  Kligman ............................ 514/559

FOREIGN PATENT DOCUMENTS 2647015  11/1990  France .

OTHER PUBLICATIONS

Chemical Abstracts 106:125,892 f (1987).
Thomas et al., "The Therapeutic Uses of Topical Vitamin A Acid,", *Journal of the American Academy of Dermatology*, 4:505-513 (1981).
A. Jarrett, "Striae Atrophicae" *Journal of Applied Cosmetology* 7:89-91 (Jul.-Sep. 1989).
M. L. Elson, "Treatment of Striae Distensae with Topical Tretinoin" *Journal Dermatological Surgery and Oncology* 16:267-270 (1990).
C. Bordier et al., "Rupture de Vergetures au Cours d'un Psoriasis Pustuleux Traite par Etretinate" *Annals of Dermatology and Venereology* 111:929-931 (1984).
P. Zheng et al., "Anatomy of Striae," *British Journal of Dermatology*, 112:185-193 (1985).

*Primary Examiner*—Leonard Schenkman
*Attorney, Agent, or Firm*—Panitch Schwarze Jacobs & Nadel

[57] ABSTRACT

Straie distensae lesions may be prevented and/or reduced in size by topically applying to the skin affected with the lesions an effective amount of retinoic acid, preferably by daily application in a dermatologically acceptable vehicle, such as a cream base, at a concentration of about 0.025 to 0.1 weight percent. When applied during the straie rubrae stage, the retinoic acid may be effective to prevent the formation of straie albae lesions, and when applied in either stage, the retinoic acid may be effective to reduce the width and depth of the lesions, with improved texture and softness.

7 Claims, No Drawings

METHODS OF PREVENTING AND REDUCING THE SIZE OF STRIAE DISTENSAE LESIONS

FIELD OF THE INVENTION

The present invention is directed to methods of preventing and/or reducing the size of lesions of striae distensae. More particularly, the invention is directed to a method of preventing the formation of striae albae and a method of reducing the size of lesions of both striae albae and striae rubrae.

BACKGROUND OF THE INVENTION

Striae distensae are very common lesions. They are present in most healthy adult women, having originated either during puberty or at the time of the first pregnancy. Stretching of the skin, as in rapid weight gain, or mechanical stress, as in weight lifting, often precedes their development. About 50 percent of pregnant women will develop these lesions, often referred to as stretch marks, on thighs, abdomen and breasts, starting at about 3 to 4 months of gestation. However, such lesions are also noted in cachectic states, for example in tuberculosis and typhoid fever, and they have also been noted after intense slimming diets.

The pathogenesis of striae distensae lesions is unclear. Some pregnant women do not develop the lesions; lesions have not been produced experimentally, and there is no animal model.

Clinicians are aware that striae distensae evolve over time passing through an early phase of inflammation (striae rubrae) and ending in the typical white stretch mark (striae albae). The striae rubrae are red, slightly elevated, linear lesions that may be tender. Later, the lesions flatten and the redness fades, leaving a permanent, wavy depression, which is the striae albae. The striae albae lesions may be 5 to 15 mm wide, depressed with a crinkly surface. These are the stretch marks which last for life, since to date there has been no known treatment.

The histopathology of striae, which always have the same appearance regardless of cause, has generated much dispute. However, P. Zheng et al., "Anatomy of Striae," *British Journal of Dermatology*, 112:185–193 (1985) present evidence that striae albae are true scars resulting from an earlier inflammatory process that destroys elastic fibers. They are not formed by stress-induced rupture of the dermal fibrous network.

Retinoic acid has been previously applied topically to the skin for the treatment of many skin disorders. See, for example the review of Thomas et al., "The Therapeutic Uses of Topical Vitamin A Acid," *Journal of the American Academy of Dermatology*, 4:505–513 (1981). It is known that tretinoin has an anti-inflammatory action useful in ameliorating chronic dermatoses such as psoriasis and lichen planus.

According to my U.S. Pat. No. 4,603,146, topical retinoic acid has been effective to stimulate formation of new collagen fibers, generate new blood vessels, correct abnormalities in elastic fibers, and eliminate neoplastic growths in chronically sundamaged skin. Retinoic acid is used world-wide to retard and reverse photodamage from excessive exposure to ultra-violet radiation in sunlight.

The literature also reports the improvement of post-acne, elevated, hypertrophic scars of the back with topical retinoic acid. These hypertrophic scars have a very different origin, following severe cystic lesions, resulting in a huge increase in collagen. In striae distensae the opposite happens; there is loss of collagen with atrophic scarring.

BRIEF SUMMARY OF THE INVENTION

According to the present invention, it has been found that striae distensae lesions may be prevented and reduced in size by applying tretinoin topically to the area of the skin affected or likely to be affected with the lesions. The retinoic acid is applied in a dermatologically acceptable vehicle, such as a cream base, preferrably in a concentration of about 0.025 to 0.1 weight percent, generally by daily application. When applied in the striae rubrae stage, the retinoic acid prevents or reduces the formation of striae albae. When applied in the striae albae stage, the scars become less noticeable, less wrinkled, and softer, though the lesions do not disappear altogether. When applied early in pregnancy before any clinical change, stretch marks may be almost completely prevented.

DETAILED DESCRIPTION OF THE PREFERRED EMBODIMENTS

Retinoic acid, also referred to as Vitamin A acid, and more particularly the all-trans isomer of retinoic acid, also known as tretinoin, is applied topically to striae distensae lesions according to the present invention. The topical application may be by spreading on with the fingers or by use of a suitable applicator such as a cotton swab.

The retinoic acid may be applied in any dermatologically acceptable vehicle such as a gel or a cream base. Retinoic acid in a cream base is available commercially for the treatment of acne from Johnson & Johnson under the trademark RETIN-A, which is available in concentrations ranging from 0.025 to 0.1 weight percent. Gel bases of RETIN-A are also available. Other suitable formulations will be apparent to those skilled in the art based upon the present disclosure.

For purposes of the present invention, the retinoic acid is generally applied in a concentration of about 0.025 to 0.1 weight percent of the total composition, and preferably about 0.25 to 0.1 weight percent of the composition. Such concentrations are too low to cause birth defects (teratogenicity). Also, concentrations of 0.1 percent or less are insufficient to cause any side effects other than some minor early irritation to which the skin gradually accommodates. No systemic effects have been reported in the treatment of many millions of acne sufferers.

Generally, the topical applications are made once daily, although twice daily or thrice weekly applications may prove beneficial or satisfactory in some cases. Clinically significant improvement is usually seen after 4 to 5 months of daily treatment. The width and depth of stretch marks is greatly reduced. Tenderness and redness are ameliorated.

For best results, the topical applications of retinoic acid are started in the early red stage (striae rubrae) in the first few months after conception. When started at this stage, not only will the lesions become narrower, shallower and much less noticeable, but permanent scarring will be largely prevented in at least about half of the patients treated. The prophylactic strategy of beginning the treatment of the invention in early pregnancy yields optimal results. The treatment should continue at least until birth, and possibly for another few months after birth, although the benefits of post-natal therapy are still being investigated.

When the topical retinoic acid treatments of the present invention are not started until the lesions have reached the striae albae stage, it is still possible to soften the scars, reduce their depth, and improve the texture of the skin with the topical applications. In these cases, the dreaded and embarrassing stretch marks can be significantly reduced in size so that they are less noticeable. Old, long-standing striae albae lesions improve only slightly.

While applicant does not wish to be bound by any particular theory, it is believed that the mechanism of action of retinoic acid in preventing and reducing the size of striae distensae is due to two actions: (1) suppression of inflammation present in striae rubra (we have shown that there is an intense inflammatory reaction in biopsies from striae rubra) and (2) stimulation of new collagen formation resulting in shallower, softer scars in both striae rubra and striae albae.

The invention will now be illustrated in further detail by reference to the following specific, non-limiting examples.

EXPERIMENTAL EXAMPLES

Over forty women with striae distensae were treated according to the present invention. The lesions on one side of the abdomen were treated with 0.05 to 0.1 percent RETIN-A cream, generally once daily, while Nivea Cream alone was applied to the other side of the abdomen as a control. Most of the forty test subjects were 3 to 5 months pregnant, showing striae rubra. The remainder had striae albae of varying duration, usually not greater than 5 years. Tretinoin was applied once daily at the start of therapy. This was sometimes increased to twice daily in those who experienced little irritation.

In the cases where treatment was begun in the striae rubrae stage, about half were greatly improved in comparison to the control. In three cases where treatment was started in the first few weeks of pregnancy before any evidence of striae distensae, the suppression of striae on the treated side was impressive (almost complete) in two of the cases. Where the treatment did not begin until the striae albae stage, about one third showed clinically significant improvement after 4 to 5 months of daily treatment. The improved women were impressed with the results. The only side effects have been some early irritation, which was temporary.

In the four cases which were biopsied, the histology showed nearly normal skin, with good collagen bundles, on the side treated with RETIN-A. The control side showed fine fibers, tightly packed in parallel array, typical of the scar.

The present invention may be embodied in other specific forms without departing from the spirit or essential attributes thereof and, accordingly, reference should be made to the appended claims, rather than to the foregoing specification as indicating the scope of the invention.

I claim:

1. A method of eliminating or reducing the size of striae distensae lesions comprising applying topically to the area of the skin affected with said lesions a composition comprising an amount of retinoic acid effective to reduce or eliminate said lesions.

2. A method according to claim 1 wherein said composition is applied about once daily to said area.

3. A method according to claim 1 wherein said composition is applied in a dermatologically acceptable vehicle at a concentration of about 0.025 to 0.1 weight percent retinoic acid.

4. A method according to claim 3 wherein said vehicle is a cream or gel base.

5. A method according to claim 1 wherein said composition is applied to the skin in the striae rubrae stage of the lesions to reduce the size of the lesions and prevent the formation of striae albae.

6. A method according to claim 1 wherein said composition is applied to the skin in the striae albae stage of the lesions to reduce the size of the lesions.

7. A method of preventing the formation of significant striae distensae of the abdomen comprising applying topically to the skin of the abdomen an effective amount of retinoic acid during early pregnancy prior to clinical appearance of lesions.

* * * * *